United States Patent [19]

Haidt

[11] 4,452,818

[45] Jun. 5, 1984

[54] EXTRAOCULAR METHOD OF TREATING THE EYE WITH LIQUID PERFLUOROCARBONS

[76] Inventor: Sterling J. Haidt, 515 South Dr., Suite 20, Mountain View, Calif. 94040

[21] Appl. No.: 359,770

[22] Filed: Mar. 19, 1982

[51] Int. Cl.$^3$ .................... A61K 31/025; A61K 31/03
[52] U.S. Cl. ...................... 424/352; 424/353
[58] Field of Search ............................. 424/352, 353

[56] References Cited

U.S. PATENT DOCUMENTS

| | | | |
|---|---|---|---|
| 3,911,138 | 10/1975 | Clark | 424/352 |
| 4,105,798 | 8/1978 | Moore et al. | 424/352 |
| 4,110,474 | 8/1978 | Lagow et al. | 424/350 |
| 4,141,973 | 2/1979 | Balazs | 424/180 |
| 4,187,252 | 2/1980 | Lagow et al. | 424/350 |
| 4,366,169 | 12/1982 | White | 424/352 |

OTHER PUBLICATIONS

Science, 152 (3730), 1755–1756 (1966).
Product Information on Healon–Pharmacia Inc., 1980.
Retina, (1981), 1 (3), 227–231.
Wellcome Trends in Ophthal., 4 (1) (1982).
Agnew Chem. Int. Ed. Engl. 17, pp. 621–634 (1978).
Label for Fluosol–DA–20%–frozen.

*Primary Examiner*—Douglas W. Robinson
*Attorney, Agent, or Firm*—Brooks, Haidt, Haffner & Delahunty

[57] ABSTRACT

Extraocular ophthalmic preparations useful as therapeutic, lubricating or protective agents are disclosed. Liquid perfluorocarbons and substituted derivatives are the active components of the ophthalmic preparations. The neat perfluorocarbon liquids are not aqueous, wherefore, isotonicity and pH need not be considered in their preparation. Liquid sterility may be maintained without the addition of preservatives. Cornea and conjunctiva surfaces are provided with greater amounts of oxygen when the perfluorocarbon liquids are employed as eye drops.

11 Claims, 2 Drawing Figures

EXTRAOCULAR METHOD OF TREATING THE EYE WITH LIQUID PERFLUOROCARBONS

BACKGROUND OF THE INVENTION

Ophthalmic preparations are administered into the eye for treating a wide variety of ocular disorders. Usually, these preparations are sterile products designed for either topical application onto the internal eyelid or instillation into the cul-de-sacs strategically positioned between the eyeball (cornea and bulba conjunctive) and eyelides (palpebral conjunctiva). Ophthalmic preparations may also be prepared in the form of an injection. At the present time, the following are the most common methods of delivering therapeutic substance to the eye: by the mechanism of some sort of vehicle or delivery system to the surface of the eye comprising ocular solutions, suspensions, ointments, gels and inserts; and by either periocular or systemic injections. If there are any diseases within the eye to be treated pharmaceutically, however, the obviously safe and most preferred method of providing that treatment would be by extraocular topical application. Some ophthalmic disorders require the replacement or augmentation of the tear film layer which may be deficient either quantitatively or qualitatively. A topical agent which would provide lubrication and protection to the external surfaces of the eye is required in these disorders. Such disorders include dry eyes syndrome caused by keratoconjunctivitis sica, tear abornalities, atrophy of the lacrimal gland, ocular pemphigoid, chemical burns, chronic keratoconjunctivitis, corneal epithelium diseases (corneal ulcers, recurrent corneal erosion and marginal ulcers), and corneal vascularization due to corneal injury, infection or transplantation.

Notwithstanding the safety and apparent convenience of topical ophthalmic preparations, several have significant disadvantages which adversely affect their efficiency and efficacy. Some of the disadvantages are inadequate persistence or retention in the cul-de-sacs, irritation, burning or stinging sensations, stickiness, and discomfort, all of which can be attributed to the vehicle, preservatives or drug itself. Because of these disadvantages, patients may not even comply with their doctor's advice for using them.

Presently, all ophthalmic preparations, including those commonly referred to as "eye drops", are required to be sterile before their instillation into the eye. In most ophthalmic preparations, sterility is achieved or maintained by incorporating preservatives. Some preservatives, however, are known to adversely affect the surface structure of the corneal epithelium and disrupt the microvilli which are necessary for the cornea to retain the tear film layer. Thus, the mucin layer of the tear film cannot be properly adsorbed onto the abnormal microvilli of the corneal and conjunctiva surfaces. Without adsorption of the mucin layer onto the corneal and conjunctiva surfaces, the wetting of these surfaces by aqueous tear film layer is hindered. Accordingly, irritation and discomfort result.

In addition to the sterility requirement, eye drops, comprising suspensions and solutions, are rapidly eliminated from the cul-de-sacs by the naso-lacrimal drainage system. As a result of their aqueous properties and low specific gravity, drops are miscible with the secretory liquids of the eye subjecting them to a faster rate of expulsion by way of the blinking mechanism. Unfortunately, their presistence in the cul-de-sacs is limited thereby significantly comprising efficiency and efficacy. Thus, to achieve therapeutic results, opthalmic eye drops require frequent administration. Because of the physical properties of suspensions, they tend to remain longer in the cul-de-sacs than solutions. Nevertheless, particles are dispersed throughout suspensions which can be irritating to the corneal and conjunctiva surfaces and frequent administration is still required.

Ophthalmic ointments and gels also cause undesirable effects when applied to the internal eyelid. Upon application, they produce a film over the corneal and conjunctiva surfaces blurring vision while usually failing to deliver a uniform dose. Moreover, they may interfere with the preocular tear film precluding its attachment to the corneal and conjunctiva surfaces. Periocular and systemic injections require an ophthalmologist not only to administer but to monitor the drug. Injections tend to cause the patient a great deal of pain and discomfort, anxiety, and inconvenience. Eye inserts provide a delivery system that maintains a low but uniform and constant delivery of a drug. Since the drug is delivered for the duration, frequent administration, as with drops, is not necessary. The major disadvantages associated with ocular inserts involve unnoticed loss of the insert from the eye, slippage of the insert into the area of sight, rupturing of the insert's membrane subjecting the delicate structures of the eye to excessive medication, possible tachyphylaxis, and structural changes in the ciliary muscle resulting from the constant exposure to the drug. Furthermore, there is some degree of manual dexterity required of the patient to position the insert therapeutically and strategically correct.

In contact lens wear, injury to the corneal epithelium may evolve as a direct consequence from the juxtaposition of the contact lens with the corneal surface. Because contact lens are required to be durable and transparent, the materials presently available for their manufacture are somewhat impermeable to oxygen and carbon dioxide as well as other small molecules. The problems observed with contact lens manufactured from these materials relates to recurrent corneal edema secondary to suboxidation of the corneal epithelium. That is, when a contact lens is positioned over the cornea, insufficient oxygen will diffuse through it, thereby irritating as well as precluding normal gaseous exchanges of the cornea. The net effect is to cause suboxidation, edema, and irritation resulting in superficial vascularization, and possible opacification of the cornea.

With respect to corneal epithelial disease, e.g., corneal ulcers and marginal corneal ulcers, there is a breakdown of the epithelial barrier which may result in infectious diseases and chronic recurrent breakdowns. The cornea, due to these disorders, will increase in hydration and loss of transparency. Thus, there is a need for proper ophthalmic preparations that can promote rapid and proper healing of such diseases to avoid formation of corneal scars or opacities. Corneal transplantation or repair is indicated when the cornea has become opaque, infiltrated, or diseased. Because the healing process, as stated above, results in corneal opacification and scars, normal vision can be partially or totally obstructed. In general, corneal transplantation or repair increases hydration while decreasing oxygenation of the cornea. Thus, an ingrowth of vessels is sometimes seen within the cornea after repair or transplantation responding to the corneal scar tissue, increase in hydration and lack of oxygen. Unfortunately, corneal repair or transplantation, as with corneal epithelial disorders, can occlude normal vision when corneal vascularization results.

It is apparent from the above brief overview of various ophthalmic preparations for the eye in pathological processes and the current state of knowledge that there are vital needs for more effective, efficacious and advantageous extraocular ophthalmic preparations.

SUMMARY OF THE INVENTION

Liquid perfluorocarbons and substituted derivatives thereof have been found to be useful as a therapeutic agent or vehicle in extraocular ophthalmic preparations. These liquids act as lubricating, wetting or protective agents, as well as vehicles for other substances or drugs. These liquids will also remain within the cul-de-sacs for greater periods of time since they have high specific gravities. In their pure state, these liquids are not aqueous, wherefore isotonicity and pH do not need to be considered. Moreover, since preservatives and materials to regulate isotonicity or pH are not required, or lesser amounts thereof are not needed to be incorporated into such liquids, irritation to the eye is minimized. Corneal and conjunctiva surfaces, when treated with such liquids, are provided with greater amounts of oxygen because of the high oxygen diffusion properties of the perfluorocarbons.

This invention is directed to the use of perfluorocarbon liquids and substituted derivatives thereof in extraocular ophthalmologic preparations. Perfluorocarbons have been found to be advantageous agents when instilled within the eye as well as a possible vehicle for other drugs and agents. Perfluorocarbon liquids have been instilled into the eye of an experimental animal as well as a human to function as a lubricant or wetting solution. They have been proven to be useful ophthalmic solutions, and the eyes of experimental animals or humans treated with this liquid maintained normal vision and demonstrated no adverse effects. Furthermore, the high specific gravity of the perfluorocarbon liquids permits their retention within the cul-de-sacs for a greater period of time. These and other remarkable discoveries will become further understood in the details which follow herein below.

The perfluorocarbon liquids preferably employed are transparent or light transmissive, stable inert, and remain viscous indefinitely. This invention is predicated in part upon the discovery that such perfluorocarbon liquids are ideal in extraocular preparations. Moreover, they dissolve oxygen and carbon dioxide extremely well, and can be sterilized by autoclaving. Thus, these liquids are comprised of unusual chemical and physical properties endowing them with unique, unexpected and advantageous uses in extraocular ophthalmic preparations. Another important discovery involved in this invention is that these perfluorocarbons can be instilled into the cul-de-sacs and will remain therein for greater periods of time because of their greater density and immiscibility with aqueous media. Also, it was found that upon blinking, a microemulsion of the perfluorocarbon liquid developed within the preocular tear film providing significant lubricating and wetting properties for the corneal and conjunctiva surfaces. Remarkably, these microemulsions remained in contact with the external surfaces of the eye for a substantial period of time. Finally, the external surface of the eye will be better oxygenated because of the perfluorocarbon's high diffusion properties for oxygen and carbon dioxide.

In another feature of the invention, perfluorocarbon liquids can be ideally employed in contact lens wear, corneal epithelial disease, and corneal transplantation and repair. For instance, the liquids will enhance oxygenation of the cornea and lubricate the epithelial surface to reduce adverse side effects associated with the contact lens use. In addition, the liquids can be applied as a protective agent in corneal epithelial diseases to prevent infection and chronic recurrent epithelial breakdowns. In corneal repair, transplantation or disease, the liquids enhance oxygenation of the corneal tissue and decrease hydration thereby reducing superficial vascularization, scar tissue and opacities.

DETAILED DESCRIPTION OF THE INVENTION

Figure 1:
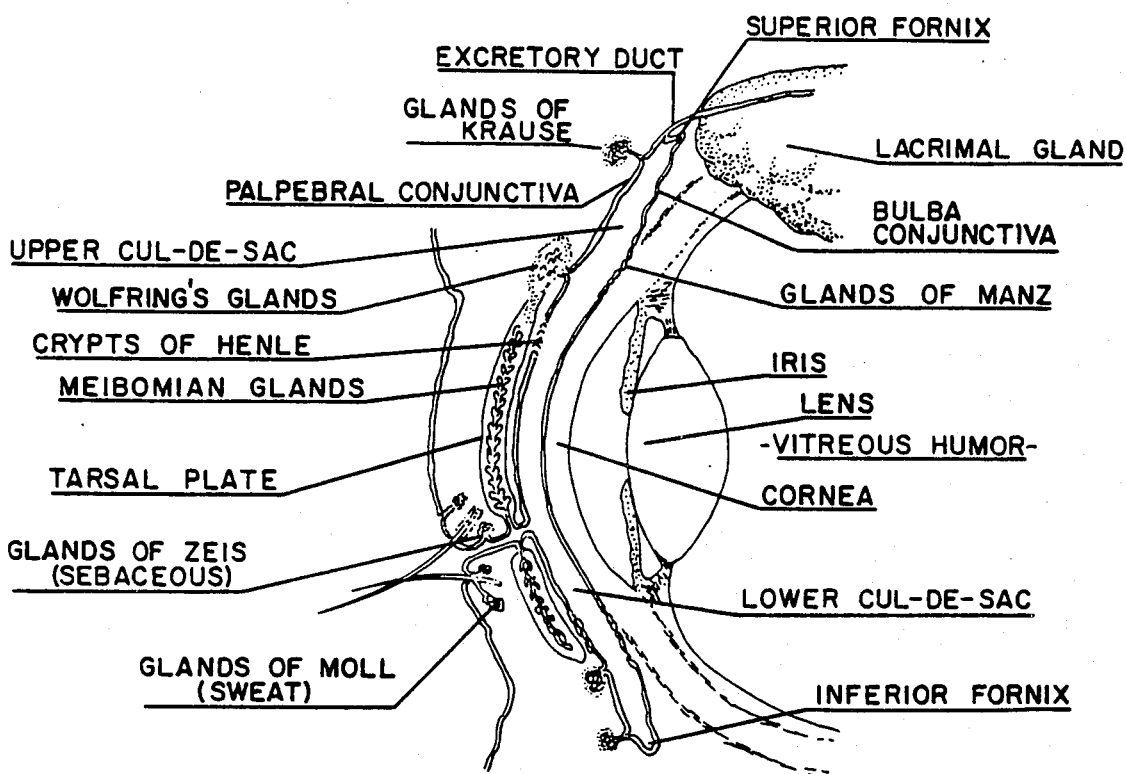

The suitable perfluorocarbons and any derivatives thereof may be generally termed as "liquids". The term "liquids", as used herein, is a comprehensive designation incorporating compounds that are in a state neither solid or gaseous such as liquids, emulsions and gels. The term "perfluorocarbon" means a "cyclic" or "acyclic" compound of carbon, whereas the term "substituted derivatives thereof" characterizes substituted perfluorocarbons with chemical elements within their structures such as oxygen, nitrogen and bromine, etc. It should also be noted that the term "perfluorocarbon" denotes substitution of all hydrogen atoms attached to the carbon atom chain or ring and any carbon side groups with fluorine. It is conceivable in the manufacture of such compounds that minor amounts of substantially fluorinated derivatives may be mixed with completely fluorinated compounds. This is permissible providing that the lack of complete replacement of all hydrogens does not affect the essential characteristics of the liquid perfluorocarbons of this invention, particularly when active hydrogens critically enhance the toxicity of the compounds. Among the perfluorocarbon compounds which may be employed are perfluorotributylamine (FC47), perfluorodecalin (PP5), perfluorotetrahydrofuran (FC80), perfluoroether (PID) [(CF$_3$)$_2$CFOCF$_2$(CF$_2$)$_2$CF$_2$OCF(CF$_3$)$_2$], perfluoroether (PIID) [(CF$_3$)$_2$CFOCF$_2$(CF$_2$)$_6$CF$_2$OCF(CF$_3$)$_2$], perfluoropolymer (E3)

perfluoropolymer (E4)

perfluoroetherpolymer (Fomblin Y/01), perfluorododecane, perfluorobicyclo[4.3.0]nonane, perfluorotrimethylcyclohexane, perfluoroisopropylcyclohexane, perfluoroendotetrahydrodicyclopentadiene, perfluoroadamantane, perfluoroexo-tetrahydrodicyclopentadiene, perfluorobicyclo[5.3.0.]decane, perfluorotetramethylcyclohexane, perfluoro-1-methyl-4-isopropylcyclohexane, perfluoro-n-butylcyclohexane, perfluorodimethylbicyclo[3.3.1.]nonane, perfluoro-1-methyl adamantane, perfluoro-1-methyl-4-t-butylcyclohexane, perfluorodecahydroacenaphthene, perfluorotrimethylbicyclo[3.3.1.]nonane, perfluoro-n-undecane, perfluorotetradecahydrophenanthrene, perfluoro-1,3,5,7-tetramethyladamantane, perfluorododecahydrofluorene, perfluoro-1,3-dimethyl adamantane, perfluoro-n-octylcyclohexane, perfluoro-7-methyl bicyclo[4.3.0.]nonane, perfluoro-p-diisopropylcyclohexane, and perfluoro-m-diisopropylcyclohexane.

It is to be understood that perfluorocarbon liquids of this invention may be formed of "neat" perfluorocarbon liquids; emulsions, suspensions or solutions of perfluorocarbons in mixture with themselves or other solvents. For instance, perfluoro-1,3-dimethyl adamantane is normally a solid but in mixture with perfluorotrimethylbicyclo[3.3.1.]nonane a liquid is formed, i.e., DAWN. The neat liquids are preferred because of their inertness and non-aqueousness. Also, when the perfluorocarbon liquids are emulsified in water, sometimes milky or even somewhat clear or transparent liquids, emulsions, gels or solutions might result which may be suitable for use in this invention. In extraocular ophthalmic preparations, fluid transparency is preferred, but even somewhat milky fluids may be used. In brief, then, the nature of the "liquid" state may include pure liquid perfluorocarbon, emulsions, solutions, suspensions, etc., of perfluorocarbon compounds in other liquid mediums. Incorporated herein by reference, therefore, are emulsions or suspensions of perfluorocarbons disclosed in U.S. Pat. Nos. 3,911,138 and 4,105,798 as suitable liquids for use in this invention.

Perfluorocarbons are capable of being synthesized by either well known chemical or electrochemical processes. The chemical processes yield fairly pure substances of known structure, having well define boiling points. Whereas the electrochemical processes tend to yield a mixture of isomers, the liquids have well defined boiling points. With respect to gas chromatography, the liquid is capable of being well defined by either the packed or capillary column procedure. The standard to define each compound in gas chromatography is prepared as follows: 2 microliters of neat liquid are added to 120 milliliters of air in a sealed bottle and allowed to vaporize producing a stock standard; upon vaporization, 120 microliters of the vapor from the stock standard are added to another 120 milliliters of air in a sealed bottle producing the working standard; the sample measured by the procedure is withdrawn from the working standard, thus, a typical sample will contain 16.7 pico liters of perfluorocarbon per milliliter of standard; however, in the capillary column procedure, the sample is split into a ratio of 23:1, therefore, only 1/23 of the sample is actually measured. As indicated in Table I, the retention time is highly definitive of the liquid used in this invention. Moreover, the capillary procedure is more specific than the packed column procedure by defining additional characteristic peaks of the compound. Thus, a more precise definition of the compound can be had with the capillary column procedure as exemplified for perfluoro 1-methyldecalin in the following TABLE.

TABLE I

| | Gas Chromatography* | |
|---|---|---|
| | Packed Column** | Capillary Column*** |
| Set Up | | |
| Standard | [16.7 pl/ml]**** | [16.7 pl/ml]**** |
| Recorder Sensitivity | 0.001v full scale | 0.001v full scale |
| Column Temperature | 100° C. | 37° C. |
| Detector Temperature | 250° C. | 250° C. |
| Injector Temperature | 150° C. | 150° C. |
| $N_2$ Gas Flow | 40 ml/min | 40 ml/min |

TABLE I-continued

| | Gas Chromatography* | |
|---|---|---|
| | Packed Column** | Capillary Column*** |
| Split | — | 23:1 |
| Recorder Speed | 2.5 cm/min | 2.5 cm/min |
| Compound | | |
| PP9 | | |
| (perfluoro 1-methyldecalin) | | |
| Attenuation | 8 | 4 |
| Sample | 50 mcl | 100 mcl |
| Peaks | 3 | 7 |
| Retention Time | | |
| $Peak_1$ | 124.8 sec. | 211.2 sec. |
| $Peak_2$ | 136.8 sec. | 240 sec. |
| $Peak_3$ | 196.8 sec. | 340.8 sec. |
| $Peak_4$ | — | 362.4 sec. |
| $Peak_5$ | — | 379.2 sec. |
| $Peak_6$ | — | 391.2 sec. |
| $Peak_7$ | — | 403.2 sec. |

*Antek 300 Gas Chromatography instrument
**Supelco, Inc. Packed Column
***Scientific Glass Engineering Capillary Column
****pl/ml = picoliters/milliliter Preferred perfluorocarbons, exemplified by perfluoro-1-methyldecalin, all have in common a high solubility for oxygen and carbon dioxide, stability inertness, high density, and transparency. They are suitable for instillation into the eye as extraocular ophthalmic preparations and in the treatment of ophthalmologic disorders. A particular perfluorocarbon or a mixture of perfluorocarbons falling within the family of liquids exemplified by the above derivative may be used according to the principles of my invention. One main property generic to the preference of the liquids according to this invention over other fluoro-containing liquids is their chemical structure rendering them RES-phobic. These compounds have been defined in U.S. Pat. No. 3,911,138 as "perfluorocyclocarbons", especially perfluoro (methylcyclohexane), perfluoro-1-methyldecalin [also known as perfluoro(decahydro-1-methylnaphthalene)], perfluoro (1,3-dimethylcyclohexane), perfluoro (decahydronaphthalene), and perfluoro (decahydrodimethylnaphthalene), or mixtures thereof, perfluorinated bicyclononane, perfluorinated bicyclooctane, perfluorinated adamantane hydrocarbon, perfluoromethyladamantane and perfluorodimethylbicyclo[3.3.1.]nonane, perfluorodimethyladamantane and perfluorotrimethylbicyclo[3.3.1.]nonane, perfluorotetrahydrodicyclopentadiene and perfluorobicyclo[5.3.0.]decane, perfluorotetrahydrodicyclopentadiene, perfluorinated bicyclononane, perfluorinated bicyclooctane, perfluorinated adamantane hydrocarbon, perfluoromethyladamantane and perfluorodimethylbicyclo[3.3.1.]nonane, perfluorodimethyladamantane and perfluorotrimethylbicyclo[3.3.1.]nonane, and perfluorotetrahydrodicyclopentadiene and perfluorobicyclo[5.3.0] decane. RES-phobic perfluorinated liquids tend to accumulate less in the bodies of animals, principally in the liver, and to a lesser extent in the spleen and kidneys. This is significant because such liquids will not become fixed indefinitely within the cells of the organ. There is another property associated with this class of perfluorocarbons that is preferentially utilized when they are introduced into the eye. A perfluorocarbon or a mixture thereof is preferably employed having a vapor pressure within the range of about 1 to about 25 torrs at about 35° C. Thus, such liquids or mixtures are not only RES-phobic, but upon escaping the cell expediently, they will not cause adverse gas collection in the tissue of animals.

In its broadest application, the method of our invention involves the instillation of liquid perfluorocarbons into the eye as extraocular ophthalmologic preparations to treat ocular disorders. The liquid can be placed or instilled in the eye by conventional eye droppers such as a dropper bottle, a separate dropper or pipette. Other means necessary to instill a gel or ointment may be used. For example, the neat liquid can be dropped into the inferior cul-de-sac, the space between the eyeball and eyelid, by tilting the head back and gently pulling down the inferior palpebral conjunctiva until a "V" pocket is formed between the eye and the inferior eyelid, whereupon the liquid or gel can be instilled into the "V" pocket. The objective is to instill the neat liquid into the inferior fornix of the inferior cul-de-sac. Because of the density, viscosity, and immiscibility of the perfluorocarbons, such liquids will sink to and remain at the inferior fornix. The mechanism of blinking will then act to disperse the liquids across the corneal and conjunctiva surfaces. The liquids, as a direct result of their immiscibility, will usually disperse as microemulsions rather than solutions. Microemulsions will be dispersed within the lipid layer of the preocular tear film acting to lubricate and wet the epithelial surfaces with a substantial amount remaining in the cul-de-sacs for significant periods of time being available for continuous dispersion. The significant retention of the liquids within the cul-de-sacs occurs as a result of their immiscibility, density and viscosity.

The eye utilizes the mechanism of blinking to not only spread the fluids therein, but also to eliminate such fluids by way of the lacrimal canaliculi. That is, the drainage of fluid, such as tears, does not depend upon gravity for its elimination, but rather, the fluid enters the puncta and passes along the lacrimal canaliculi by capillary attraction aided by aspiration caused by a contraction of muscle embedded within the eyelids. When the eyelids are partially closed, as in the initial phase of blinking, contraction of the muscles causes the puncta to close. The canaliculi are then compressed while the lacrimal sac is dilated when the eyelids are further closed. Fluid, thus, is aspirated into the sac and forced down the nasolacrimal duct toward its aperture into the nose. When a perfluorocarbon liquid is dropped into the eye, the mechanism of blinking is less efficient in its elimination. This effect is due to the density, viscosity, and immiscibility of these liquids which act to antagonize the aspiration effect of blinking, retarding their expulsion. Perfluorocarbon liquids, as extraocular ophthalmology preparations, are beneficial for treating dry eyes and tear abnormalities such as aqueous tear deficiency, tear film instability, surfacing problems, and the effects of irritants. Upon dispersion of the prefluorocarbon liquids across the corneal and conjunctiva surfaces, the microemulsions are dispersed within the lipid or outermost layer of the tear film where it will primarily demonstrate its effect. There should be little if no adverse effects on the mucin layer, as seen with ointments, when such liquids are instilled. Thus, the instillation of perfluorocarbon liquids as extraocular ophthalmology preparations will provide a lubricating, wetting or protecting surface without interfering with mucin adsorption onto the corneal and conjunctiva surfaces. Thus, the liquids will not only provide these beneficial effects on the pre-ocular tear film, but will remain within the cul-de-sacs for longer periods of time as a result of their immiscibility, density and viscosity. In contrast to these advantageous liquid perfluorocarbons, the present ocular lubricants which include solutions of hydroxypropyl methylcellulose, polyvinyl alcohol, polyvinyl pyrrolidine soluble polymers, dextran and mixtures thereof which are rapidly cleared from the eye require frequent administration.

No preservatives are necessary to maintain sterility in the preferred preparations of the invention because neat perfluorocarbons are nonaqueous. Thus, the microvilli within the epithelial of the cornea are not adversely effected, as exhibited by present extraocular ophthalmic preparations, and the absorption of mucin onto the microvilli remain intact. Since the liquids are non-aqueous, the pH or isotonicity does not have to be considered to avoid irritation and stinging upon their instillation. With contact lenses, the liquids can be employed as protective, wetting, lubricating and oxygenating extraocular ophthalmic preparations. The irritation and possible superficial vascularization and opacification of the cornea will also be reduced. In corneal epithelial diseases, such as corneal ulcers, recurrent corneal erosion and marginal corneal ulcers, the liquid perfluorocarbon preparations will decrease the incidence of corneal vacularization, scarring and opacification as seen with such corneal disorders. Likewise, in corneal repair and transplantation, the application of perfluorocarbon liquids during and after such procedures should decrease or eliminate the untoward side effects of corneal vacularization, scarring and opacification. It is the oxygen-carrying property of the liquid perfluorocarbons as well as their non-aqueous, viscous, and dense properties that make them ideal liquids to treat such procedures.

Due to the retention of perfluorocarbon liquids within the eye for considerable periods of time, such liquids can be employed as suitable vehicles for other substances. Presently drops, ointments, and ocular inserts are utilized to deliver drugs extraocularly. As stated above, solutions and suspensions are readily excreted, the preparations available may contain irritants, ointments blur vision and interfere with mucin adsorption, while ocular inserts are uncomfortable and subject to rupture or loss. With the use of liquid perfluorocarbons as vehicles, the number of administrations can be reduced while the adverse effects of ointments, suspensions and inserts are eliminated.

In view of the above description, it is apparent that perfluorocarbon liquids and derivatives thereof are unique and advantageous liquids when used in extraocular ophthalmological preparations. The invention, its principles and objectives will be further understood in view of the following examples with reference to the drawings which are anatomical illustrations of the eye.

FIG. 1 constitutes a vertical section of the eye illustrating the eyelid, and the external and internal components of the eye. As stated, the secretory components of the eye secrete the preocular tear film which is comprised of three layers. The oil layer originates from the meibomian glands and glands of Zeis, the aqueous layer is produced by the lacrimal and accessory lacrimal (Wolfring's and Krause) glands, while mucin is made by the goblet cells (not illustrated) which are scattered over the palpebral conjunctiva. The superior and inferior fornix constitute the deposit area within the superior and inferior cul-de-sacs. The middle layer, the tear fluid, is aqueous and provides hydration, antibacterial agents and nutritional elements to the external surfaces. The innermost layer of the tear film comprises mucin which covers the conjunctiva and corneal surfaces. Mucin functions to permit the overlying aqueous layer to spread across the surfaces. Herein the term "external surface" of the eye is meant to include broadly all such surfaces shown in the drawing and referred to herein which may come into direct contact with liquid which is introduced between an eyelid and eyeball.

Figure 2:
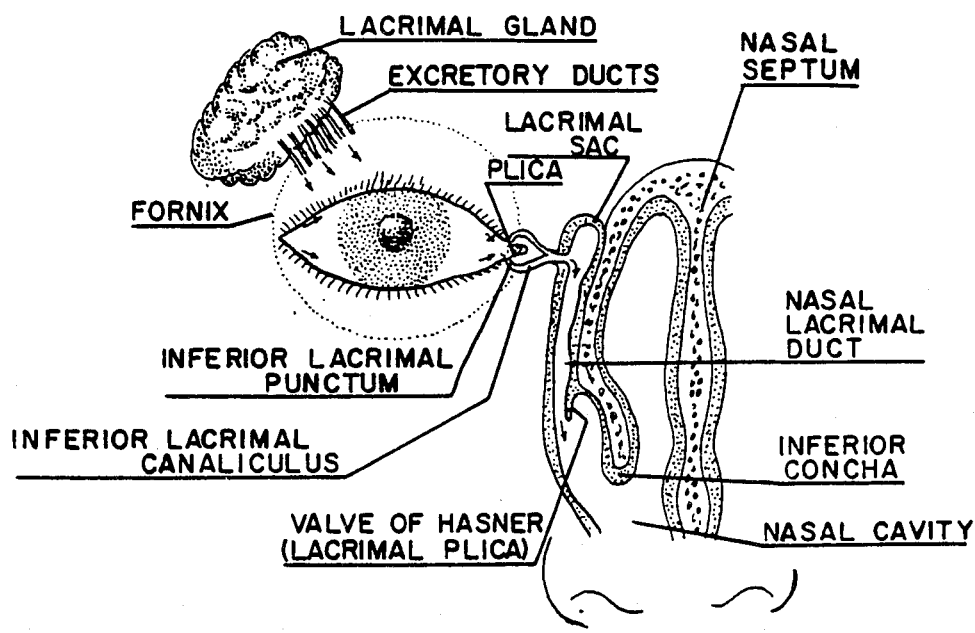

FIG. 2 illustrates the excretory apparatus employed by the eye to eliminate fluids therein. The puncta are the apertures leading into the lacrimal canaliculus and eventually into the nasal lacrimal duct.

EXAMPLE I

A single drop from a 3 ml syringe and a 25 gauge needle containing perfluoro 1-methyldecalin (PP9) was instilled, i.e., placed into each eye of a rabbit. The rabbit was observed for a period of two hours through a Codman-Mentor Operating Microscope. Specifically, the examination of the rabbit cornea showed no evidence of corneal toxicity as manifested by the lack of epithelial staining and maintenance of corneal transparency. Also, there was no inflammation or irritation observed in the bulbar or palpebral conjunctiva. Further, the rabbit demonstrated no abnormal visual responses.

EXAMPLE II

A single drop containing perfluoro-1-methyldecalin (PP9), was instilled into the right eye of a human. The instillation, using a plastic dropper bottle, was made onto the interior cul-de-sac of the right eye. Prior to and after instilling the liquid, various tests including Visual Acuity, Corneal Sensitivity, Anterior Segment Examination with and without Fluoroscein, Rose Bengal and Tear Film stability were conducted for comparative purposes. No negative effects or results were found before or after the instillation of the perfluoro-1-methyldecalin. Thus, the results demonstrated that the eye remained unchanged after the experiment. The subject's visual acuity, as measured before and after, was 20/20 corrected. There was no change in his corneal sensitivity. The slit-lamp biomicroscopy test with and without fluorescein and with and without Rose Bengal detected no corneal ulcers, irritations or drying cells on his ocular surface. The subject's tear stability or break-up time, also measured before and after, remained the same at 25 seconds. Furthermore, the subject experienced no gritty, stringing, or burning sensations, or excess mucous secretions from the instilled liquid. The subject found the liquid to be comfortable, soothing and did not interfere with his blinking or vision. The liquid was detected in his eye for up to an hour after it had been instilled. Finally, there were no ocular, nasal, or gastointestinal side effects experienced by the subject.

In view of the above detailed description and examples, other modifications will become apparent to those of ordinary skill in the art to which this invention pertains.

What is claimed is:

1. A method for treating the eyes and providing lubrication and protection to the surface of the eye which comprises topically applying to the eye a composition comprising as an essential ingredient a transparent or light transmissive, stable, inert, viscous perfluorocarbon or substituted derivative thereof having oxygen carrying properties in an amount sufficient to act as a lubricant.

2. The method of claim 1 wherein said liquid is a perfluorocyclocarbon.

3. The method of claim 2 wherein said perfluorocyclocarbon is selected from the group consisting of perfluoro(mthylcyclohexane), perfluoro(1,3-dimethylcyclohexane), perfluoro(decahydronaphthalene), perfluoro(decahydro-1-methylnaphthalene), perfluoro(decahydrodimethylnaphthalene), perfluorodimethyladamantane, perfluorotrimethylbicyclo[3.3.1.]nonane, perfluorotetrahydrodicyclopentadiene, perfluorobicyclo[5.3.0.]decane and perfluorodimethylbicyclo[3.3.1.]nonane, or mixtures thereof.

4. The method of claim 1 wherein said perfluorocarbon is perfluoro-1-methyldecalin.

5. A method of claim 1 wherein said eye contains a contact lens.

6. A therapeutic method as defined in claim 1 wherein said composition is applied topically by instilling said composition into an eye cul-de-sac.

7. A therapeutic method as defined in claim 1 wherein said composition is dispersed across the corneal and conjunctiva surfaces of the eye.

8. A therapeutic method as defined in claim 1 wherein said composition also contains a pharmaceutical agent present in a therapeutically effective amount.

9. A therapeutic method as defined in claim 1 wherein said composition is in a form selected from the group consisting of a neat liquid, an emulsion, an ointment, a gel, a solution, and a suspension.

10. A therapeutic method as defined in claim 5 wherein said composition is dispersed to the corneal epithelium prior to inserting the contact lens onto the corneal epithelium.

11. A therapeutic method as defined in claim 5 wherein said composition has been applied to the contact lens after or before the contact lens has been inserted onto the corneal epithelium.

* * * * *

UNITED STATES PATENT AND TRADEMARK OFFICE
CERTIFICATE OF CORRECTION

PATENT NO. : 4,452,818

DATED : June 5, 1984

INVENTOR(S) : STERLING J. HAIDT

It is certified that error appears in the above-identified patent and that said Letters Patent is hereby corrected as shown below:

Col. 1, line 11, "bulba conjunctive" should read
--bulba conjunctiva--

Col. 7, line 55, "prefluorocarbon" should read
--perfluorocarbon--

Col. 8, line 13, "absorption" should read --adsorption--

In the Claims - Claim 3, line 20

"perfluoro(mthylcyclohexane)," should read
--perfluoro(methylcyclohexane),--

Signed and Sealed this

Fifteenth Day of January 1985

[SEAL]

Attest:

GERALD J. MOSSINGHOFF

Attesting Officer   Commissioner of Patents and Trademarks